(12) United States Patent
Minami et al.

(10) Patent No.: US 8,236,575 B2
(45) Date of Patent: Aug. 7, 2012

(54) CARRIER FOR ANALYSIS OF AN ANALYTE AND PROCESS FOR PRODUCING THE SAME

(75) Inventors: Koichi Minami, Ashigarakami-gun (JP); Hirohiko Tsuzuki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 12/744,311

(22) PCT Filed: Nov. 21, 2008

(86) PCT No.: PCT/JP2008/003434
§ 371 (c)(1),
(2), (4) Date: May 21, 2010

(87) PCT Pub. No.: WO2009/066469
PCT Pub. Date: May 28, 2009

(65) Prior Publication Data
US 2010/0290954 A1    Nov. 18, 2010

(30) Foreign Application Priority Data
Nov. 22, 2007  (JP) ................................ 2007-303026

(51) Int. Cl.
*G01N 33/543* (2006.01)
(52) U.S. Cl. ......... 436/518; 435/7.1; 436/501; 436/524; 436/525; 436/526; 436/527; 436/528; 436/529; 436/530; 436/531; 436/532; 436/535; 422/68.1; 422/69
(58) Field of Classification Search ............... 422/68.1, 422/69; 435/501, 528–535, 547; 436/7.1, 436/7.5–7.9, 7.92, 7.94
See application file for complete search history.

(56) References Cited

U.S. PATENT DOCUMENTS

| | | | |
|---|---|---|---|
| 3,996,345 A * | 12/1976 | Ullman et al. ................ | 436/537 |
| 6,689,574 B1 | 2/2004 | Cummings | |
| 2007/0087195 A1 | 4/2007 | Meyer et al. | |
| 2008/0261829 A1 * | 10/2008 | Harvey et al. .................. | 506/13 |

FOREIGN PATENT DOCUMENTS

| JP | 2001-519525 A | 10/2001 |
|---|---|---|
| JP | 2002-311031 A | 10/2002 |
| JP | 2006-138656 A | 6/2006 |
| JP | 2007-040834 A | 2/2007 |
| JP | 2007-523754 A | 8/2007 |
| JP | 2008-083042 A | 4/2008 |

(Continued)

OTHER PUBLICATIONS

Extended European Search Report Mar. 17, 2011; Appln. No. 08851758.6-1223/2224241.

(Continued)

*Primary Examiner* — Melanie J Yu
*Assistant Examiner* — Erik B Crawford
(74) *Attorney, Agent, or Firm* — Sughrue Mion, PLLC (57) ABSTRACT

A first reactant, which is provided with a reaction site for specific binding with an analyte, and a fluorescent label site, and a second reactant, which is provided with a reaction site for specific binding with the analyte, and a fluorescence recognition site for recognizing fluorescence produced by the fluorescent label site of the first reactant, are respectively fixed onto a support such that the first reactant and the second reactant have a positional relationship adapted for the binding with the analyte.

6 Claims, 2 Drawing Sheets

FOREIGN PATENT DOCUMENTS

| | | |
|---|---|---|
| WO | 2004106890 A2 | 12/2004 |
| WO | 2006063031 A2 | 6/2006 |
| WO | 2007/015509 A1 | 2/2007 |

OTHER PUBLICATIONS

Jong-Ho Kim, et al., "Polymeric nanoparticles for protein kinase activity", Chem. Commun., 2007, No. 13, pp. 1346-1348.

Kazuko Hirayama, et al., "Synthesis of polymer particles with specific binding sites for lysozyme by a molecular imprinting technique and its application to a quartz crystal microbalance sensor", Journal of Japan Society for Analytical Chemistry, 2000, pp. 29 to 33, vol. 49, No. 1.

Nicholas W. Turner, et al., "Formation of protein molecular imprints within Langmuir monolayers: A quartz crystal microbalance study", Journal of Colloid and Interface Science, 2007, pp. 71-80, vol. 308, No. 1.

Koichi Minami, et al., "Novel molecular imprinting technology utilizing antibody variable region fragments", 2008, p. 1, 1P-1346.

\* cited by examiner

CARRIER FOR ANALYSIS OF AN ANALYTE AND PROCESS FOR PRODUCING THE SAME

TECHNICAL FIELD

This invention relates to a carrier for analysis of an analyte, wherein fluorescence resonance energy transfer is utilized. This invention also relates to a process for producing the carrier for analysis of an analyte.

BACKGROUND ART

Heretofore, as techniques for detecting a protein, immunological analysis techniques utilizing an antibody with respect to the protein have been utilized widely. For example, with an ELISA technique, an object protein is quantitatively analyzed with a high sensitivity. Also, with a Western blotting technique, excellent separation competence of electrophoresis and high specificity of an antigen-antibody reaction are combined with each other, and a specific protein is thereby detected from a protein mixture. Further, in cases where a labeled antibody is caused to act upon a tissue sample, a localized state of an object protein within a tissue or within a cell is observed.

However, with the immunochemistry techniques described above, it is necessary to perform complicated operations, such as an antibody binding operation and a subsequent washing operation.

As techniques for observing movement of a protein within an organism, techniques utilizing various fluorescent proteins, typically a green fluorescent protein (GFP), have been known. The fluorescent proteins may be formed within an organism by genetic engineering and are therefore useful for observation of the localized state of an endogenous protein within a tissue or within a cell and the movement of the endogenous protein.

However, with the aforesaid techniques utilizing the fluorescent proteins, the object protein must be formed within the viable cell in the form having previously been fused with the fluorescent protein, and it is not always possible to visualize an exogenous antigen within the cell.

Various studies have been conducted for solving the problems described above. For example, a fluorescence resonance energy transfer technique, or the like, is often utilized for analysis of spatial close positions of labeled biomolecules or molecule groups in a biological system. The fluorescence resonance energy transfer technique is useful as means for verification with respect to various biological reactions or interactions, which are objects of interest, such as a protein-protein interaction, an antigen-antibody reaction in an immune reaction, a receptor-ligand interaction, hybridism of nucleic acid, and binding of a protein to nucleic acid.

In patent literature 1, a technique is described, wherein an immunological analysis reagent containing an antigen and an antibody, which have been joined together by a linker and have respectively been labeled with fluorescent substances, is used, and wherein detection is made on a real time basis in accordance with a competitive reaction with an exogenous antigen. It is described that, with the immunological analysis reagent described above, in cases where the competing exogenous antigen is not present, the fluorescence resonance energy transfer (FRET) arises due to the formation of an antigen-antibody complex. It is also described that, in cases where the competing exogenous antigen is present, since the competing exogenous antigen is bound with the antibody and since the FRET does not arise, the presence or absence of the exogenous antigen is detected quickly and in a simple manner.

However, with the technique described in patent literature 1, wherein the antigen-antibody complex is not fixed by a support, the problems occur in that a washing operation is not capable of being performed, and that the immunological analysis reagent diffuses and flows out little by little in an unclosed space. Therefore, the immunological analysis reagent is capable of being utilized only one time, and it is not always possible to use the immunological analysis reagent in applications in which the immunological analysis reagent is to be utilized repeatedly. Also, since the detection with the competition technique is made, the sensitivity is apt to become bad and is not sufficient for the detection of a trace quantity of the antigen. Further, the competition technique, wherein an analysis is made by later adding a different reagent, is not suitable for the analysis, for example, within the organism. Furthermore, in cases where two kinds of reactants are joined together via a linker as in the technique described in patent literature 1, the problems occur in that, since the linker must be designed at the time of every joining operation such that the reactants may act efficiently, antigen flexibility is lost, and the production cost becomes high. For repetitive utilization, the linker may be removed, and the two kinds of the reactants may be separated from each other and merely fixed to the support. In such cases, the distance between a YFP acting as a first luminous substance and a CFP acting as a second luminous substance is not capable of being rendered close. If a fixation quantity of the YFP and the fixation quantity of the CFP are increased for rendering the YFP and the CFP close to each other, the problems will occur in that the large quantity of the YFP and the large quantity of the CFP become close to each other, and in that a signal-to-noise ratio becomes markedly low.

As a technique for fixing an antigen onto a solid layer by the utilization of the antigen-antibody reaction, a technique referred to as molecular imprinting is disclosed in, for example, patent literature 2. Specifically, it is described that a molecular imprint gel is obtained with processing, wherein a complex of a monomer or a polymer, into which a ligand with respect to an object molecule has been introduced, and the object molecular are subjected to a reaction with a polymeric crosslinking agent, where a gel containing a complex of the ligand and the object molecule is thereby prepared, and wherein the object molecule is then removed from the gel. Also, it is disclosed that, in cases where an AFP acting as an antigen is added to a gel carrier, which contains an anti-AFP antibody and lectin, the gel contracts due to the binding of the anti-AFP antibody and lectin with the AFP. It is described that the presence of the AFP (the object molecule) is detected in accordance with the swelling and the contraction of the gel.

However, since the antigen-antibody complex is fixed to the support by polymerization, in order for the antigen to arrive at the antibody, the antigen must enter into the crosslinked gel matrix structure. Therefore, a long time is required before the antigen and the antibody undergo the reaction. In order for the substance to be recognized reliably, the antigen in a markedly high concentration must be brought into contact with the antigen-antibody complex for a length of time ranging from two hours to four hours. Also, for the same reasons, at the time of washing and removal of the antigen, the antigen is not capable of being removed efficiently, and response characteristics are apt to become bad. Therefore, in cases where the fluorescence resonance energy transfer technique is applied to the molecular imprinting technique described above, since an alteration in distance between a fluorescent label site and a fluorescence recognition site for recognition of the fluorescence, which is produced by the fluorescent label site, is markedly slow, the problems occur in that the fluorescent label site and the fluorescence recognition site are always in a close state as for a short length of time (for example, a length of time of approximately five minutes), in that an alteration in fluorescence intensity is thus not capable of being analyzed, and in that the detection is not made quickly and with a high sensitivity.

Patent literature 1:
 Japanese Unexamined Patent Publication No. 2007-40834
Patent literature 2:
 Japanese Unexamined Patent Publication No. 2006-138656

DISCLOSURE OF INVENTION

Problems which the Invention Aims at Solving

As described above, none of the aforesaid techniques provides a carrier sufficient as a carrier for analysis of an analyte, which carrier enables an object molecule to be analyzed quickly with a high sensitivity and in a simple manner, and which carrier is usable repeatedly even after a washing operation.

Also, in the cases of use of a carrier as a biosensor, there has been a strong demand for a process for producing a carrier for analysis of an analyte, which process has a high flexibility in application from a view point of a production cost.

In view of the above circumstances, the object of the present invention is to provide a carrier for analysis of an analyte, which carrier enables an analyte to be detected quickly with a high sensitivity and in a simple manner by use of fluorescence resonance energy transfer, chemical amplification type luminescence, or the like, on a solid layer without a competitive reaction being used, and which carrier is usable repeatedly even after a washing operation.

Another object of the present invention is to provide a process for producing a carrier for analysis of an analyte, which process enables the carrier for analysis of an analyte to be produced with a high flexibility in application and efficiently without a linker design being required.

Means for Solving the Problems

The present invention provides a carrier for analysis of an analyte, comprising:
 i) a support,
 ii) a first reactant, which is provided with:
 a reaction site for specific binding with an analyte, and
 a fluorescent label site, and
 iii) a second reactant, which is provided with:
 a reaction site for specific binding with the analyte, and
 a fluorescence recognition site for recognizing fluorescence produced by the fluorescent label site of the first reactant,
 the first reactant and the second reactant being respectively fixed onto the support such that the first reactant and the second reactant have a positional relationship adapted for the binding with the analyte.

The carrier for analysis of an analyte in accordance with the present invention should preferably be modified such that a polymer layer is formed on the support, and the first reactant and the second reactant are fixed onto the support via the polymer layer. The polymer layer should preferably have a layer thickness falling within the range of 1 nm to 0.5 mm.

Also, the carrier for analysis of an analyte in accordance with the present invention should preferably be modified such that the polymer layer is fixed onto the support via a self-assembled monolayer. The self-assembled monolayer should preferably have a layer thickness falling within the range of 0.2 nm to 10 μm.

The polymer layer should preferably be a polysaccharide layer.

Further, the carrier for analysis of an analyte in accordance with the present invention should preferably be modified such that each of the first reactant and the second reactant is selected from the group consisting of an antibody and an analyte-binding fragment. Furthermore, the carrier for analysis of an analyte in accordance with the present invention should preferably be modified such that the fluorescent label site of the first reactant is selected from the group consisting of a fluorescent dye and fluorescent protein. Also, the carrier for analysis of an analyte in accordance with the present invention should preferably be modified such that a reaction occurring between the fluorescent label site of the first reactant and the fluorescence recognition site of the second reactant is fluorescence resonance energy transfer. Further, the carrier for analysis of an analyte in accordance with the present invention should preferably be modified such that the analyte is an antigen.

The carrier for analysis of an analyte in accordance with the present invention is appropriate as a carrier for use as a biosensor or a bioreactor.

The present invention also provides a process for producing a carrier for analysis of an analyte, comprising the steps of:
 i) allowing an analyte, a first reactant, and a second reactant to react with one another,
 the first reactant being provided with a reaction site for specific binding with the analyte, and a fluorescent label site,
 the second reactant being provided with a reaction site for specific binding with the analyte, and a fluorescence recognition site for recognizing fluorescence produced by the fluorescent label site of the first reactant,
 a binding product of the first reactant, the analyte, and the second reactant being obtained from the reaction, and
 ii) imparting the binding product to a surface of a support, whereby the first reactant and the second reactant are respectively fixed to the surface of the support.

The process for producing a carrier for analysis of an analyte in accordance with the present invention should preferably be modified such that, after the first reactant and the second reactant have been respectively fixed to the surface of the support, the analyte is removed from the binding product.

Also, the process for producing a carrier for analysis of an analyte in accordance with the present invention should preferably be modified such that the removal of the analyte from the binding product is performed under conditions such that the binding of the analyte is weakened.

Effects of the Invention

The carrier for analysis of an analyte in accordance with the present invention comprises: (i) the support, (ii) the first reactant, which is provided with the reaction site for the specific binding with the analyte, and the fluorescent label site, and (iii) the second reactant, which is provided with the reaction site for the specific binding with the analyte, and the fluorescence recognition site for recognizing the fluorescence produced by the fluorescent label site of the first reactant, the first reactant and the second reactant being respectively fixed onto the support such that the first reactant and the second reactant have the positional relationship adapted for the binding with the analyte.

Therefore, with the carrier for analysis of an analyte in accordance with the present invention, in cases where a washing operation is performed on the carrier, there is no risk of the first reactant and the second reactant flowing out from the carrier.

Also, with the carrier for analysis of an analyte in accordance with the present invention, the first reactant and the second reactant are respectively provided with the reaction sites for the specific binding with the analyte and are respectively fixed as two independent reactants onto the support such that the first reactant and the second reactant have the positional relationship adapted for the binding with the analyte. Therefore, in cases where the analyte is present, the first reactant and the second reactant quickly and easily undergo the binding with the analyte. At the time at which the first reactant and the second reactant recognize the analyte, the efficiency, with which the fluorescence is recognized, alters. Therefore, by the analysis of the alteration quantity of the fluorescence recognition efficiency, the concentration of the analyte is analyzed accurately and in a simple manner. Also, since the first reactant and the second reactant are fixed to the support, in cases where the washing operation is performed on the carrier, diffusion and flowing out of the first reactant and the second reactant do not arise, and the repeated analysis becomes possible.

Further, with the carrier for analysis of an analyte in accordance with the present invention, wherein the detection is made with the technique other than the competition technique, a trace quantity of the analyte is analyzed with a high sensitivity. Furthermore, it is sufficient for the first reactant and the second reactant to be respectively provided with the reaction sites for the specific binding with the analyte, and the linker designing for every analyte as in patent literature 1 need not be performed. Also, with respect to the labeling with a fluorescent substance, processing wherein an identical molecule is labeled with the fluorescent substance or the fluorescence recognition substance, selectively, need not be performed. Therefore, with the carrier for analysis of an analyte in accordance with the present invention, the first reactant and the second reactant need not be joined by a linker. Accordingly, the carrier for analysis of an analyte in accordance with the present invention is applicable to every antigen-antibody combination. Further, labeling operations may be performed as independent operations. Thus the carrier for analysis of an analyte in accordance with the present invention has the advantages in that the flexibility is markedly high, and the producibility is excellent.

BEST MODE FOR CARRYING OUT THE INVENTION

Figure 1:
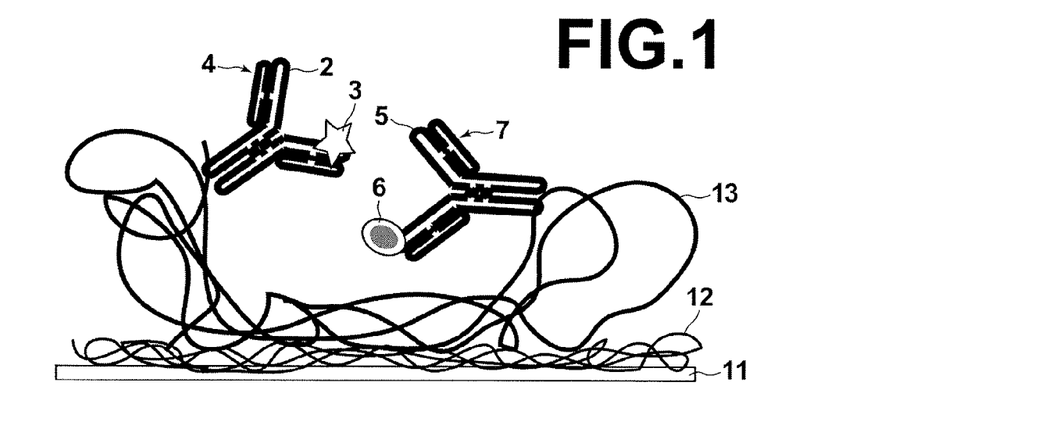
FIG. 1 is a schematic explanatory view showing an embodiment of the carrier for analysis of an analyte in accordance with the present invention.

The present invention will hereinbelow be described in further detail with reference to the accompanying drawings. FIG. 1 is a schematic explanatory view showing an embodiment of the carrier for analysis of an analyte in accordance with the present invention. As illustrated in FIG. 1, the carrier for analysis of an analyte in accordance with the present invention comprises a first reactant 4, which is provided with a reaction site 2 for specific binding with an analyte, and a fluorescent label site 3. The carrier for analysis of an analyte in accordance with the present invention also comprises a second reactant 7, which is provided with a reaction site 5 for specific binding with the analyte, and a fluorescence recognition site 6 for recognizing the fluorescence produced by the fluorescent label site 3 of the first reactant 4. The first reactant 4 and the second reactant 7 are respectively fixed onto a support 11 such that the first reactant 4 and the second reactant 7 have a positional relationship adapted for the binding with one piece of the analyte. Specifically, a silane coupling layer 12 and a hydrogel 13 are formed in this order on the support 11, and the first reactant 4 and the second reactant 7 are respectively fixed to the hydrogel 13.

In the embodiment illustrated in FIG. 1, the silane coupling layer 12 and the hydrogel 13 are formed in this order on the support 11, and the first reactant 4 and the second reactant 7 are fixed to the hydrogel 13. In accordance with the material of the support 11, the silane coupling layer 12 and the hydrogel 13 may not be formed on the support 11. Alternatively, only either one of the silane coupling layer 12 and the hydrogel 13 may be formed on the support 11.

The fluorescent label site 3 of the first reactant 4 and the fluorescence recognition site 6 of the second reactant 7, which site recognizes the fluorescence produced by the fluorescent label site 3 of the first reactant 4, are the sites between which the fluorescence resonance energy transfer occurs. The fluorescence resonance energy transfer is the phenomenon, in which excitation energy transfers between two fluorescent dyes varying in excitation wavelength (i.e., between the fluorescent label site 3 of the first reactant 4 and the fluorescence recognition site 6 of the second reactant 7). Also, the first reactant 4 and the second reactant 7 are respectively fixed onto the support 11 such that the first reactant 4 and the second reactant 7 have the positional relationship adapted for the binding with the analyte. Therefore, in cases where the reaction site 2 of the first reactant 4 and the reaction site 5 of the second reactant 7 have been bound with the analyte, the fluorescent label site 3 of the first reactant 4 and the fluorescence recognition site 6 of the second reactant 7 become close to each other and take the positions spaced by a close distance that allows the fluorescence resonance energy transfer to occur.

Figure 2:
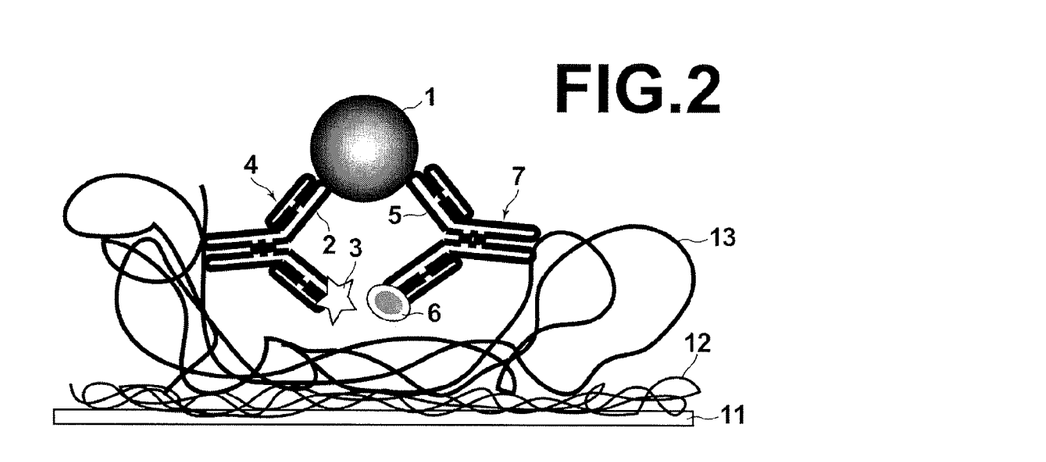
FIG. 2 is a schematic explanatory view showing a state, in which a first reactant and a second reactant have been bound with an analyte in the embodiment of FIG. 1.

The aforesaid fluorescence resonance energy transfer will further be described with reference to FIG. 2. FIG. 2 is a schematic explanatory view showing a state, in which a first reactant and a second reactant have been bound with an analyte in the embodiment of FIG. 1. In FIG. 2 (and those that follow), similar elements are numbered with the same reference numerals with respect to FIG. 1. Explanations for the similar elements will hereinbelow be omitted in so far as the explanations are not necessary particularly. In cases where an analyte 1 is added to the carrier for analysis of an analyte illustrated in FIG. 1, the reaction site 2 for the specific binding with the analyte 1, which reaction site is of the first reactant 4, and the reaction site 5 for the specific binding with the analyte 1, which reaction site is of the second reactant 7, respectively undergo the specific binding with the analyte 1. Therefore, the fluorescent label site 3 of the first reactant 4 and fluorescence recognition site 6 of the second reactant 7 become close to each other, and the fluorescence resonance energy transfer occurs between the fluorescent label site 3 of the first reactant 4 and fluorescence recognition site 6 of the second reactant 7. As a result, the fluorescence produced by the fluorescent label site 3 of the first reactant 4 decreases, and the fluorescence at the fluorescence recognition site 6 of the second reactant 7 increases. Therefore, by observation of an alteration in fluorescence intensity before the analyte 1 is added and after the analyte 1 has been added, the detection (the analysis) of the analyte 1 is made.

In the embodiment described above, the reaction occurring between the fluorescent label site 3 of the first reactant 4 and fluorescence recognition site 6 of the second reactant 7 is the fluorescence resonance energy transfer. However, the reaction occurring between the fluorescent label site 3 of the first reactant 4 and fluorescence recognition site 6 of the second reactant 7 is not limited to the fluorescence resonance energy transfer and may be, for example, chemical amplification type luminescence, wherein the first reactant excites an oxygen molecule, and wherein the recognition site of the second reactant is caused to emit light by singlet state oxygen.

Figure 3:
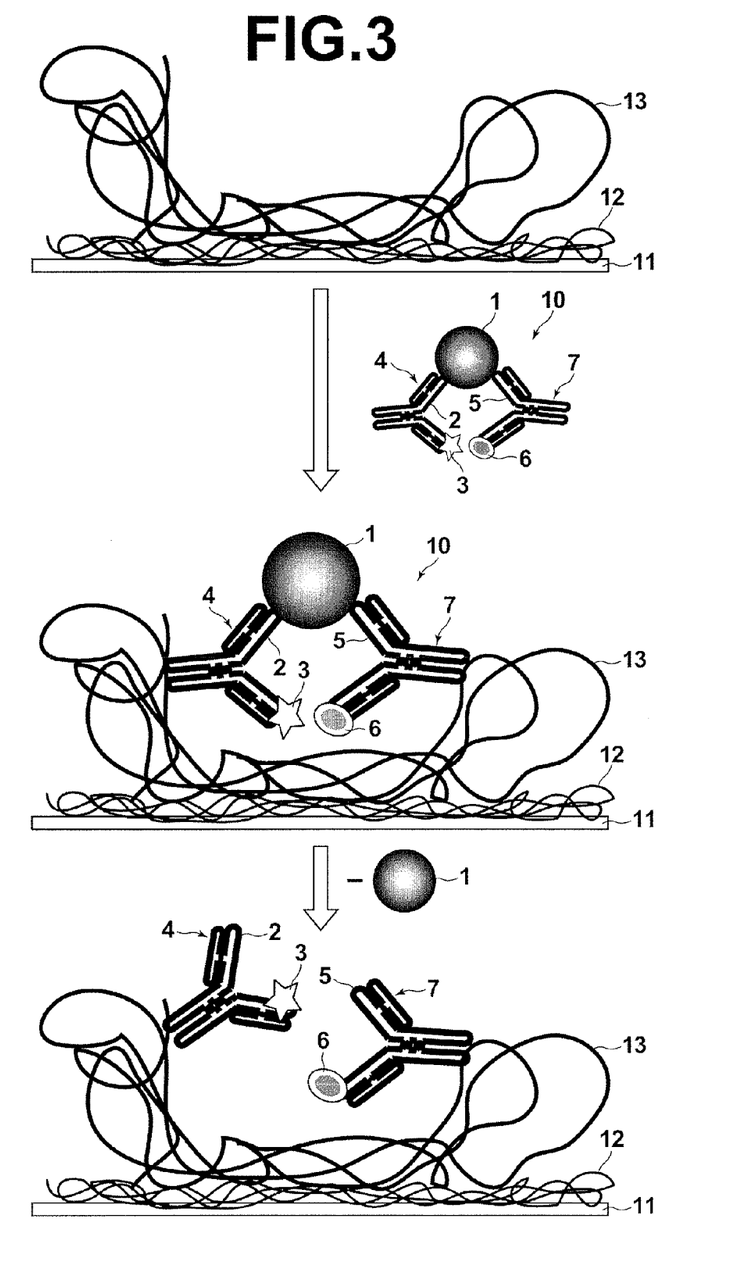
FIG. 3 is a flow diagram showing steps of an embodiment of the process for producing a carrier for analysis of an analyte in accordance with the present invention.

An embodiment of the process for producing a carrier for analysis of an analyte in accordance with the present invention will be described hereinbelow with reference to FIG. 3. The carrier for analysis of an analyte in accordance with the present invention is obtained with processing, wherein a binding product of the first reactant, the analyte, and the second reactant is formed, wherein the binding product is imparted and fixed to the support on which the hydrogel has been fixed, and wherein the analyte is then removed from the binding product.

Since the first reactant 4 and the second reactant 7 are provided respectively with the reaction site 2 and the reaction site 5 for the specific binding with the analyte 1, a binding product 10 of the first reactant 4, the analyte 1, and the second reactant 7 is obtained with processing, wherein the first reactant 4, the analyte 1, and the second reactant 7 are mixed together in arbitrary proportions in an aqueous solution.

Thereafter, the binding product 10 is added to the surface of the support 11 and is allowed to undergo an appropriate reaction. The binding product 10 is thus fixed to the surface of the support 11. At this time, the reaction site 2 of the first reactant 4 and the reaction site 5 of the second reactant 7 are protected by being bound with the analyte 1, and therefore a particular protection processing need not be performed. Techniques for binding the binding product with the support will be obvious to experts in the art. For example, in cases where the surface of the support has a carboxyl group, a technique maybe employed, wherein the surface of the support is activated with an activating agent, such as EDC, which will be described later, and wherein the fixation is thereby performed. Also, a technique may be employed, wherein a maleimido group is imparted to the surface of the support, wherein a thiol group of the first reactor and/or the second reactor is allowed to react with the surface of the support, and wherein the fixation is thereby performed. In this invention, the binding technique is not limited to those described above, and an arbitrary binding technique may be employed.

In cases where the carrier for analysis of an analyte in accordance with the present invention is used for a biosensor, the fixation quantity (density) of the binding product, which is bound on the support, should preferably fall within the range of 1 piece/mm$^3$ to $1\times10^{18}$ pieces/mm$^3$, should more preferably fall within the range of $1\times10^9$ pieces/mm$^3$ to $1\times10^{15}$ pieces/mm$^3$, and should most preferably fall within the range of $1\times10^{13}$ pieces/mm$^3$ to $1\times10^{14}$ pieces/mm$^3$. In cases where the density is to be obtained through measurement, after the binding product has been fixed to the support, the analyte may be washed, and the quantity of the fluorescence produced by the fluorescent label substance of the first reactant and the quantity of the fluorescence produced by the fluorescent label substance of the second reactant may be measured. Also, the film thickness may be measured by AFM or ellipsometry, and the density may then be obtained by calculation.

In order for the carrier for analysis of an analyte in accordance with the present invention as illustrated in FIG. 1 to be obtained, after the binding product 10 has been fixed onto the support 11, the analyte 1 may be removed from the binding product 10. The removal of the analyte 1 from the binding product 10 should preferably be performed under conditions, such that the binding of the reaction site 2 of the first reactant 4 and the analyte 1 with each other and the binding of the reaction site 5 of the second reactant 7 and the analyte 1 with each other are weakened, and such that the binding of the first reactant 4 and the support 11 with each other and the binding of the second reactant 7 and the support 11 with each other are not weakened. Specifically, a washing operation may be performed on the carrier for analysis of an analyte. At this time, since the first reactant 4 and the second reactant 7 have respectively been independently fixed to the support 11, the analyte 1 is removed easily. Also, the reproducibility of the binding with the analyte 1 at the time of the use as the fixation carrier does not become bad.

The removal of the analyte 1 is performed easily by use of an appropriate washing liquid. The washing liquid used in this case may be a liquid which weakens the binding force of the analyte 1. Examples of the conditions for weakening the binding force include the pH alteration to the acidic side or the alkaline side, and an increase of a salt concentration. The conditions for weakening the binding force vary in accordance with the kinds of the first reactant 4, the second reactant 7, and the analyte 1, and the like. For example, it is possible to use an acidic glycine buffer for adjusting the pH value at a value of at most 2, an alkaline NaOH solution for adjusting the pH value at a value of at least 10, or a borate buffer for adjusting the salt concentration at a value of at least 0.5M. It is also possible to use an arginine-containing acidic buffer, a guanidine-containing buffer, or the like. The period of time, during which the washing processing with the washing liquid is performed, may be adjusted appropriately. From the view point of eliminating adverse effects upon the binding activity of the first reactant 4 and the second reactant 7, ordinarily, the period of time, during which the washing processing with the washing liquid is performed, may be at most 10 minutes, and should preferably be at most one minute. From the view point of the reproducibility, the period of time, during which the washing processing with the washing liquid is performed, should preferably be at least five seconds.

The constituent elements, such as the support, of the embodiment of the carrier for analysis of an analyte in accordance with the present invention as illustrated in FIG. 1, and the analyte will be described hereinbelow. Thereafter, how the embodiment of the carrier for analysis of an analyte in accordance with the present invention as illustrated in FIG. 1 is applied to the biosensor and the bioreactor will be described.

(1) Support

Ordinarily, the support employed in the present invention may be constituted of one of various materials, e.g., optical glass, such as BK7; silica; metal oxides, such as alumina, titania, zirconia, and indium tin oxide (ITO); metal nitrides, such as silicon nitride, gallium nitride, aluminum nitride, and indium nitride; and synthetic resins, such as a sepharose, a polyethylene, a polystyrene, a poly(meth)acrylic acid, a poly(meth)acrylamide, a polymethyl(meth)acrylate, a polyethylene terephthalate, a polycarbonate, and a cycloolefin polymer. The above-enumerated materials for the support should preferably be imparted with a functional group. Particularly, the support should preferably be constituted of a material, which is transparent with respect to light, such as glass, the ITO, the polymethyl(meth)acrylate, the polyethylene terephthalate, the polycarbonate, and the cycloolefin polymer. Examples of the functional groups include an amino group, a carboxyl group, a maleimido group, an aldehyde group, a succinimido group, a thiol group, a hydrazine group, an isocyanate group, an epoxy group, a vinyl sulfone group, a vinyl group, and a cyano group.

The support should more preferably be constituted of a material, which does not exhibit anisotropy with respect to polarization and has good processability.

As a technique for imparting the functional groups described above, it is possible to employ one of various known surface processing techniques, such as plasma processing, ozone processing, acid or alkali etching processing, and self-assembled monolayer processing. From the view point of the producibility, the self-assembled monolayer processing should preferably be employed.

(2) Polymer Layer

The polymer layer is bound with the support. The polymer layer may be constituted of a hydrophilic polymer, a hydrophobic polymer, or a combination of the hydrophilic polymer and the hydrophobic polymer with each other, and should preferably be constituted of the hydrophilic polymer alone. The polymer layer may be bound directly or indirectly with the support. In cases where the polymer layer is to be bound directly with the support, for example, a technique may be employed, wherein the polymer is bound with the support through graft polymerization. In cases where the polymer layer is to be bound indirectly with the support, for example, a technique may be employed, wherein a hydrophobic polymer is applied onto the support, and wherein a hydrophilic polymer is then bound with the hydrophobic polymer. It is also possible to employ a technique, wherein a compound (hereinbelow referred to as the linker) capable of binding with the support and the polymer is applied to the surface of the support, and wherein the polymer layer is then bound with the linker. It is particularly preferable to employ a technique, wherein the self-assembled monolayer is used as the linker, and wherein the hydrophilic polymer is bound via the self-assembled monolayer with the glass support. The particularly preferable technique will be described hereinbelow.

(2-1) Self-assembled Monolayer

Examples of the techniques for forming the self-assembled monolayer include <1> a technique using a silane coupling agent, and <2> a technique using an alkanethiol. Each of the techniques for forming the self-assembled monolayer will be described hereinbelow.

<1> Technique Using a Silane Coupling Agent

With respect to a base material comprising a metal oxide or a metal nitride, such as silica or silicon nitride, or a thin film of the metal oxide or the metal nitride, the polymer layer may be bound via a silane coupling layer having been formed by the silane coupling agent. As the silane coupling agent, it is possible to use a silicon-containing compound that is represented by the general formula A-1 shown below, wherein $X^a$ represents a functional group, $L^a$ represents a linker moiety containing a straight, branched, or cyclic carbon chain, $R^a$ represents hydrogen or an alkyl group having one to six carbon atoms, $Y^a$ represents a hydrolyzable group, and each of m and n represents an integral number falling within the range of 0 to 3, with the proviso that m+n=3. A covalent bond expressed as support (silicon)-oxygen-silicon-carbon is thus formed on the surface of the support, and the surface of the base material is thereby covered with the functional group.

$$X^a\text{-}L^a\text{-Si}\text{—}(R^a_m)Y^a_n \qquad \text{A-1}$$

Examples of the hydrolyzable groups ($Y^a$) include an alkoxy group, a halogen, and an acyloxy group. Specifically, examples of the hydrolyzable groups ($Y^a$) include a methoxy group, an ethoxy group, and chlorine. The hydrolyzable group ($Y^a$) should preferably be the methoxy group or the ethoxy group. Examples of the silane coupling agents include γ-aminopropyltrimethoxysilane, N-β(aminoethyl) γ-aminopropyltrimethoxysilane, γ-aminopropylmethyldiethoxysilane, γ-mercaptopropyltrimethoxysilane, and γ-glycidoxypropyltriethoxysilane. The reaction of the silane coupling agent may be performed in accordance with an ordinary procedure, e.g. the procedure described in a book "Effects and Usage of Silane Coupling Agents" (published by Science & Technology Co.).

The functional group ($X^a$) which the silane coupling agent has may be selected from a wide variety of functional groups, which bind with polymers and binding products described later. As the functional group ($X^a$), it is possible to utilize an arbitrary functional group, such as an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group, a maleimido group, a combination of two or more of the above-enumerated functional groups, and derivatives of the above-enumerated functional groups. The functional group ($X^a$) should preferably be the amino group or the epoxy group.

<2> Technique Using an Alkanethiol

With the technique using the alkanethiol, a metal film is located on the aforesaid support, and thereafter the alkanethiol is imparted. The term "located on a support" as used herein embraces the cases wherein the metal film is located on the support so as to be in direct contact with the support, and the cases wherein, instead of being in direct contact with the support, the metal film is located on the support via a different layer. Examples of the metals for constituting the metal film include free electron metals, such as gold, silver, copper, aluminum, and platinum. The metal for constituting the metal film should preferably be gold. Each of the above-enumerated metals may be used alone, or at least two kinds of metals among the above-enumerated metals may be used in combination. Also, with adhesion characteristics with respect to the support being taken into consideration, an intervening layer constituted of chromium, or the like, may be located between the support and the layer constituted of the metal.

The film thickness of the metal film may be set at an arbitrary value. The film thickness of the metal film should preferably fall within the range of 0.1 nm to 500 nm, and should more preferably fall within the range of 1 nm to 200 nm. In cases where the intervening layer constituted of chromium, or the like, is located between the support and the metal film, the thickness of the intervening layer should preferably fall within the range of 0.1 nm to 10 nm.

A technique for covering a metal film by use of the alkanethiol has been developed vigorously by Professor Whitesides of Harvard University, et al. The details of the technique for covering a metal film by use of self-assembled monolayers have been reported in, for example, Chemical Review, 105, 1103-1169 (2005). In cases where gold is employed as the metal, an alkanethiol, which may be represented by the general formula A-2 shown below, wherein n represents an integral number falling within the range of 3 to 20 and wherein $X^b$ represents a functional group, may be used as the organic layer forming compound. In such cases, a monolayer having orientational characteristics is formed in a self-assembled manner in accordance with van der Waals force of the Au—S bond and the alkyl group with each other. The self-assembled monolayer is prepared with a markedly simple technique, wherein the gold support is dipped in a solution of the alkanethiol derivative. Specifically, for example, the self-assembled monolayer may be formed by use of the compound, which may be represented by the general formula A-2, wherein $X^b$ represents an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group, or a maleimido group. The functional group is thus capable of being imparted to the support surface.

$$HS(CH_2)_n X^b \qquad \text{A-2}$$

In the general formula A-2, the repetition number (n) of the alkyl group should preferably be an integral number falling within the range of 3 to 16, and should more preferably be an integral number falling within the range of 4 to 8. Also, the alkyl group moiety may be substituted by a multiple bond or a heteroatom, such as nitrogen or oxygen. If the alkyl chain of the alkanethiol derivative is markedly short, the self-assembled monolayer will not always be capable of being formed. If the alkyl chain of the alkanethiol derivative is markedly long, the solubility in water will become low, and handling characteristics will become bad.

Further, the self-assembled monolayer is capable of being formed by use of the alkanethiol, which may be represented by the general formula A-2, wherein the functional group $X^b$ represents only one kind of the functional group. Furthermore, the self-assembled monolayer is capable of being formed by use of a mixture of the alkanethiol, which may be represented by the general formula A-2, and other kinds of alkanethiols.

By use of the linker described above, it is possible to produce the support having the surface provided with the functional group ($X^a$) or the functional group ($X^b$). The linker need not necessarily be the self-assembled monolayer and may be a compound, which is capable of imparting the functional group ($X^a$) or the functional group ($X^b$) to the surface of the support.

The self-assembled monolayer may have an arbitrary layer thickness. The layer thickness of the self-assembled monolayer should preferably fall within the range of 0.2 nm to 10 μm, should more preferably fall within the range of 1 nm to 500 nm, and should most preferably fall within the range of 5 nm to 50 nm. In cases where the layer thickness of the self-assembled monolayer is equal to at most 10 μm, it becomes possible for the analyte to diffuse easily through the layer. In cases where the layer thickness of the self-assembled monolayer is equal to at least 0.2 nm, it becomes possible for the fixation quantity of the fixation object substance to be kept large.

Also, in the present invention, the first reactant and the second reactant may be fixed directly to the self-assembled monolayer described above. From the view point of the enhancement of the analyte binding rate of the first reactant and the second reactant, the carrier for analysis of an analyte in accordance with the present invention should preferably have a constitution, wherein the polymer layer is formed on the self-assembled monolayer, and wherein a functional group for fixation of the first reactant and the second reactant is thereby imparted to the surface of the support.

(2-2) Polymer

As the polymer, which may be employed in the present invention, a hydrophilic polymer should preferably be used. Examples of the hydrophilic polymers, which may be employed in the present invention, include gelatin, agarose, chitosan, dextran, carrageenan, alginic acid, starch, cellulose, and derivatives of the above-enumerated hydrophilic polymers, such as carboxymethyl derivatives; and water-swelling organic polymers, such as a polyvinyl alcohol, a polyacrylic acid, a polyacrylamide, a polyethylene glycol, and derivatives of the above-enumerated water-swelling organic polymers.

As the hydrophilic polymer, which may be employed in the present invention, it is also possible to use a carboxyl group-containing synthetic polymer or a carboxyl group-containing polysaccharide. Examples of the carboxyl group-containing synthetic polymers include a polyacrylic acid, a polymethacrylic acid, and copolymers thereof, e.g. copolymers as described in Japanese Unexamined Patent Publication No. 59 (1984)-53836, page 3, line 20 to page 6, line 49, and Japanese Unexamined Patent Publication No. 59 (1984)-71048, page 3, line 41 to page 7, line 54, such as a methacrylic acid copolymer, an acrylic acid copolymer, an itaconic acid copolymer, a crotonic acid copolymer, a maleic acid copolymer, a partially esterified maleic acid copolymer, and an addition product of a polymer having a hydroxyl group and an acid anhydride. The carboxyl group-containing polysaccharide may be an extract from a natural plant, a product of microorganism fermentation, a synthetic product obtained with an enzyme, or a chemical synthetic product. Examples of the carboxyl group-containing polysaccharides include hyaluronic acid, chondroitin sulfate, heparin, dermatan sulfate, carboxymethyl cellulose, carboxyethyl cellulose, cellouronic acid, carboxymethyl chitin, carboxymethyl dextran, and carboxymethyl starch. As the carboxyl group-containing polysaccharide, it is possible to use a commercially available compound. Examples of the commercially available compounds include CMD (carboxymethyl dextran), CMD-L, and CMD-D40 (which are supplied by Meito Sangyo Co., Ltd.); sodium carboxymethyl cellulose (which is supplied by Wako Pure Chemical Industries, Ltd.); and sodium alginate (which is supplied by Wako Pure Chemical Industries, Ltd.).

No limitation is imposed upon a weight-average molecular weight of the hydrophilic polymer employed in the present invention. Ordinarily, the weight-average molecular weight of the hydrophilic polymer employed in the present invention should preferably fall within the range of $2 \times 10^2$ to $5 \times 10^5$, and should more preferably fall within the range of $1 \times 10^4$ to $2 \times 10^6$. If the weight-average molecular weight of the hydrophilic polymer is smaller than the range described above, the fixation quantities of the reactants will become small. If the weight-average molecular weight of the hydrophilic polymer is larger than the range described above, the handling characteristics will become bad due to a high solution viscosity.

As for the hydrophilic polymer, the film thickness of the hydrophilic polymer in an aqueous solution should preferably fall within the range of 1 nm to 0.5 mm, should more preferably fall within the range of 1 nm to 1 μm, and should most preferably fall within the range of 100 nm to 500 nm. If the film thickness is markedly small, the fixation quantity of the physiologically active substance will become small, and the interaction with the sample substance will not be always capable of occurring. If the film thickness is markedly large, there will be the risk that the uniformity of the hydrophilic polymer is not kept. The film thickness of the hydrophilic polymer in the aqueous solution is capable of being evaluated with AFM, ellipsometry, or the like.

(2-3) Activation of the Polymer

In cases where the polymer containing the carboxyl group is used as the aforesaid polymer, with a technique for activating the carboxyl group, the polymer is capable of being fixed to the surface of the support. As the technique for activating the polymer containing the carboxyl group, it is possible to use appropriately a known technique, e.g., a technique for activating with 1-(3-dimethylaminopropyl)-3-ethylcarbodiimide (EDC), which is a water-soluble carbodiimide, and N-hydroxysuccinimide (NHS), or a technique for activating with EDC alone. In cases where the polymer containing the carboxyl group, which polymer has been activated with the technique described above, is caused to react with the support having the amino group, the hydrophilic polymer is capable of being bound on the support.

Also, as the technique for activating the polymer containing the carboxyl group, it is possible to use a technique wherein a nitrogen-containing compound is utilized. Specifically, it is possible to utilize a nitrogen-containing compound represented by the general formula (Ia) or the general formula (Ib) shown below, wherein each of $R^1$ and $R^2$ independently represents a carbonyl group, a carbon atom, or a nitrogen atom, which may have a substituent group, or $R^1$ and $R^2$ jointly represent a five-membered ring or a six-membered ring, A represents a carbon atom or a phosphorus atom, which has a substituent group, M represents an (n-1)-valent element, and X represents a halogen atom.

In this case, each of $R^1$ and $R^2$ may independently represent a carbonyl group, a carbon atom, or a nitrogen atom, which may have a substituent group. Preferably, $R^1$ and $R^2$ jointly represent the five-membered ring or the six-membered ring. Particularly preferably, there is furnished hydroxysuccinic acid, hydroxyphthalic acid, 1-hydroxybenzotriazole, 3,4-dihydroxy-3-hydroxy-4-oxo-1,2,3-benzotriazine, and derivatives of the above-enumerated compounds.

It is also possible to utilize preferably the nitrogen-containing compounds, which may be represented by the formulas shown below.

Further, as the nitrogen-containing compound, it is possible to utilize preferably the compound, which may be represented by the general formula (I) shown below, wherein each of Y and Z independently represents CH or a nitrogen atom.

General formula (I)

Preferable examples of the compounds, which may be represented by the general formula (I), include the compounds, which may be represented by the formulas shown below.

Furthermore, as the nitrogen-containing compound, it is possible to utilize preferably the compound, which may be represented by the formula shown below.

Also, as the nitrogen-containing compound, it is possible to utilize preferably the compound, which may be represented by the general formula (II) shown below, wherein A represents a carbon atom or a phosphorus atom, which has a substituent group, each of Y and Z independently represents CH or a nitrogen atom, M represents an (n-1)-valent element, and X represents a halogen atom.

General formula (II)

In this case, the substituent group, which the carbon atom or the phosphorus atom has, should preferably be an amino group having a substituent group, and should more preferably be a dialkylamino group, such as a dimethylamino group, or a pyrrolidino group. The (n-1)-valent element, which is represented by M, may be, for example, a phosphorus atom, a boron atom, or an arsenic atom, and should preferably be the phosphorus atom. The halogen atom, which is represented by X, may be a fluorine atom, a chlorine atom, a bromine atom, or an iodine atom, and should preferably be the fluorine atom.

Preferable examples of the compounds, which may be represented by the general formula (II), include the compounds, which may be represented by the formulas shown below.

Further, as the nitrogen-containing compound, it is possible to utilize preferably the compound, which may be represented by the general formula (III) shown below, wherein A represents a carbon atom or a phosphorus atom, which has a substituent group, M represents an (n-1)-valent element, and X represents a halogen atom.

General formula (III)

A preferable example of the compound, which may be represented by the general formula (III), is the compound, which may be represented by the formula shown below.

Further, as the technique for activating the polymer containing the carboxyl group, it is possible to use preferably a technique wherein a phenol derivative, which has an electron-attracting group, is utilized. In such cases, the electron-attracting group should preferably have the σ value of at least 0.3. Specifically, it is possible to utilize, for example, the compounds, which may be represented by the formulas shown below.

The carbodiimide derivative described above may be utilized in combination with the nitrogen-containing compound or the phenol derivative. Alternatively, when necessary, each of the carbodiimide derivative described above, the nitrogen-containing compound, and the phenol derivative may be utilized alone. There should preferably be utilized the combination of the carbodiimide derivative and the nitrogen-containing compound.

Also, as the technique for activating the polymer containing the carboxyl group, it is possible to use a technique wherein the compound, which may be represented by the formula shown below, is utilized. The compound, which may be represented by the formula shown below, may be utilized alone or in combination with the carbodiimide derivative, the nitrogen-containing compound, and/or the phenol derivative.

Further, as the technique for activating carboxylic acid in the polymer containing the carboxyl group, it is possible to use preferably a technique described in Japanese Unexamined Patent Publication No. 2006-58071, [0011] to [0022] (i.e., the technique, wherein a carboxyl group located on a surface of a support is activated by use of a compound selected from the group consisting of a uranium salt, a phosphonium salt, and a triazine derivative, which have specific structures, and wherein a carboxylic acid amido group is thereby formed). It is also possible to use preferably a technique described in Japanese Unexamined Patent Publication No. 2006-90781, [0011] to [0019] (i.e., the technique, wherein a carboxyl group located on a surface of a support is activated by use of a carbodiimide derivative or a salt thereof, wherein esterification is performed by use of a compound selected from the group consisting of a nitrogen-containing heteroaromatic compound having a hydroxyl group, a phenol derivative having an electron-attracting group, and an aromatic compound having a thiol group, wherein a reaction with an amine is performed, and wherein a carboxylic acid amido group is thereby formed).

(2-4) Application of the Polymer to the Support

In the present invention, in cases where the polymer containing the carboxyl group is used as the aforesaid polymer, the polymer containing the carboxyl group having been activated may be caused to undergo the reaction with the support in the form of a solution. Alternatively, the polymer containing the carboxyl group having been activated may be applied to form a thin film on the support by use of a technique, such as a spin coating technique, and may be caused to undergo the reaction with the support in the state of the thin film. The polymer should preferably be caused to undergo the reaction with the support in the state of the thin film.

As described above, in the present invention, the polymer containing the carboxyl group having been activated should preferably be caused to undergo the reaction with the support in the state of the thin film. As the technique for forming the thin film on the support, one of known techniques may be employed. Specifically, it is possible to employ an extrusion coating technique, a curtain coating technique, a casting technique, a screen printing technique, a spin coating technique, a spray coating technique, a slide beads coating technique, a slit and spin technique, a slit coating technique, a die coating technique, a dip coating technique, a knife coating technique, a blade coating technique, a flow coating technique, a roll coating technique, a wire bar boating technique, a transfer printing technique, or the like. The thin film forming techniques are described in, for example, "Coating Gijutsu No Shinpo" (Progress of Coating Technology), written by Yuji Harasaki, Sogo Gijutsu Center (1988); "Coating Gijutsu" (Coating Technology), Technical Information institute Co., Ltd. (1999); "Suisei Coating No Gijutsu" (Aqueous Coating Technology), CMC (2001); "Shinka Suru Yuki Hakumaku Seimaku-Hen" (Evolving Organic Thin Film, Film Formation Edition), Sumibe Techno Research Co., Ltd. (2004); and "Kobunshi Hyomen Kako Gaku" (Polymer Surface Processing Engineering), written by Akatsuki Iwamori, Gihodo Shuppan (2005). In the present invention, as the technique for forming the thin film on the support, the spray coating technique or the spin coating technique should preferably be employed, and the spin coating technique should more preferably be employed. With the spray coating technique or the spin coating technique, a coating film having a controlled film thickness is capable of being prepared easily.

(3) First Reactant and Second Reactant

In the present invention, each of the first reactant and the second reactant is provided with the reaction site for the specific binding with the analyte. Specifically, each of the first reactant and the second reactant is an antibody or an analyte-binding fragment. Examples of the antibodies or the antigen-binding fragments thereof include an antibody molecule itself, and an artificial single chain antibody having the binding characteristics with the corresponding antigen, such as a Fab fragment, a F(ab')$_2$ fragment, or an ScFV (single chain fragment of variable region) constructed by joining a variable regions of an L chain and an H chain, respectively, of an antibody with each other. The single chain antibody is capable of being formed in a prokaryon cell, such as a coli bacillus, and in a cell, such as a plant cell, which is other than the cell of a mammal. The single chain antibody is preferable since the single chain antibody has a small volume, and since the fluorescence resonance energy transfer occurs easily. Also, each of the L chain and the H chain of the antibody may be used as a combination of the first reactant or the second reactant. Techniques for preparing the single chain antibody, such as the ScFV, are well known. It is sufficient for the antibody or the antigen-binding fragment thereof used in the present invention to have the binding characteristics by the antigen-antibody reaction with the analyte (antigen) described later. The antibody or the antigen-binding fragment thereof used in the present invention is not necessarily limited to the antibody, which is obtained with the antigen acting as an immunogen, or the antigen-binding fragment of the antibody. The antibody employed in the present invention is the antibody undergoing the antigen-antibody reaction with the analyte.

The term "fluorescence recognition" as used herein broadly embraces the cases where light emission or a chemical reaction occurs through the direct excitation from the excited state of a fluorescent substance or through indirect excitation. In the present invention, each of the first reactant and the second reactant may be labeled with a fluorescent substance. Alternatively, only the label antibody may be labeled with the fluorescent substance. In cases where each of the first reactant and the second reactant is labeled with the fluorescent substance, each of the first reactant and the second reactant may be labeled at an arbitrary site in so far as the binding with the antigen or the binding with the antibody is not affected adversely. The fluorescence recognition site of the second reactant for the recognition of the fluorescence produced by the fluorescent substance need not necessarily be constituted of the fluorescent substance and may be constituted of a substance which is usable repeatedly.

As described above, in cases where light having excitation wavelengths is irradiated to the fluorescent label site of the first reactant, the fluorescence resonance energy transfer occurs at the time, at which the fluorescent label site of the first reactant and the fluorescence recognition site of the second reactant take the positions spaced by a close distance from each other. As a result, the fluorescence of the fluorescent label site of the first reactant decreases, and the fluorescence of the fluorescence recognition site of the second reactant increases. In cases where the fluorescent label site of the first reactant and the fluorescence recognition site of the second reactant take the positions spaced away from each other, the fluorescence resonance energy transfer ceases. As a result, the fluorescence of the fluorescent label site of the first reactant increases, and the fluorescence of the fluorescence recognition site of the second reactant decreases.

The term "fluorescence" as used herein embraces the light emitted by a molecule in the excited state, which molecule has been formed by a chemical reaction, as in the cases of phosphorescence and the light emission of luminol. Examples of the aforesaid molecules include luminous organism-derived luciferins, such as a firefly (*Photinus pyralis*) luciferin, a sea-firefly (*Cypridina*) luciferin, a sea pansy (*Renilla reniformis*) luciferin, a luminous earthworm (*Diplocardia*) luciferin, a latia (*Latia neritoides*) luciferin, a firefly squid (Wataseniae) luciferin, and a bacterial luciferin (reduction type flavin mononucleotide); and Aequorin derived from a bowl jellyfish (*Aequarea victoria*).

The fluorescence resonance energy transfer described above is well known as described in PCT Japanese Publication No. 2007-523754, [0158] to [0161], and PCT Japanese Publication No. 2001-519525, [0025]. Various kinds of fluorescent dyes for the fluorescence resonance energy transfer (the fluorescent label site of the first reactant and the fluorescence recognition site of the second reactant) are available commercially. The combination of the fluorescent label site and the fluorescence recognition site may be selected from a wide variety of combinations such that the fluorescence resonance energy transfer occurs between the fluorescent label site and the fluorescence recognition site. The fluorescent substances for the fluorescent label site and the fluorescence recognition site may be selected arbitrarily from those described in literatures and those available commercially. Examples of the fluorescent substances for the fluorescent label sites and the fluorescence recognition sites include a fluorescein derivative, a Rhodamine derivative, an aminocoumarin derivative, a hydroxycoumarin derivative, a BODIPY derivative, an anthracene derivative, a benzofuran derivative, a porphyrine derivative, Cy Dye, Alexa Fluor, europium cryptate, DyLight, HiLyte Fluor, Oyster, MegaStokes Dye, an IRDye fluorescent dye, and fluorescent proteins, such as a DFP, a YFP, a GFP, and a BFP.

In cases where the fluorescence resonance energy transfer is utilized in the present invention, it is desirable that the energy transfer occurs between the selected fluorescent substances, and that the state, in which the energy transfer has occurred, is stable. It is possible to use preferably a combination of fluorescent proteins or fluorescent dyes, such as GFP-YFP, Alexa Fluor 555-Alexa Fluor 647, or F1TC-Alexa Fluor 555. The combination may be the combination of the fluorescent proteins, the combination of the fluorescent dyes, or the combination of the fluorescent dye and the fluorescent proteins. The combination is not limited to the examples described above. From the view point of the stability of the fluorescence production, the fluorescent substance should preferably be Alexa Fluor or HiLyte Fluor, and should more preferably be Alexa Fluor.

The fluorescence resonance energy transfer between the CFP and the YFP, and the fluorescence resonance energy transfer between the GFP and the BFP or between the modification products thereof are known widely. The fluorescent proteins described above are available commercially. In cases where the fluorescent protein is used, it is possible to produce a single-molecule fusion protein by the joining with the antibody to be labeled, or the like (the antibody or the antigen-binding fragment thereof). Also, in cases where the fluorescent protein is used in a viable cell, a gene for coding the fusion protein may be introduced. Therefore, in cases where the fluorescent substance is to be used in the viable cell, it is convenient to use the fluorescent protein. Nucleic acids for coding the fluorescent proteins are well known, and various kinds of vectors containing the nucleic acids are available commercially. Therefore, a fluorescent label protein, in which the fluorescent protein has been fused with a desired polypeptide, is capable of being prepared easily by the utilization of the commercially available vector.

A technique for labeling the antibody, or the like, with the fluorescent dye, may be selected appropriately in accordance with the kind of the fluorescent dye used. In cases where the fluorescent dye is a nonpeptide compound, the labeling with the fluorescent dye may be performed with a known technique, such as a chemical modification technique wherein a reducing group, such as a maleimido group, is imparted to a thiol group or an amino group of the antibody. In cases where the fluorescent dye is a peptide compound, such as the fluorescent protein, it is possible to produce the fusion protein with the antibody, or the like, as described above. The technique for producing the fusion protein will be described later in the example in accordance with the present invention. However, the technique for producing the fusion protein is not limited to the technique described in the example in accordance with the present invention and may be selected from various known techniques.

The fluorescent dye, which the first reactant has, and the fluorescent dye, which the second reactant has, are bound at the positions such that the fluorescence resonance energy transfer occurs at the time at which the aforesaid antibody, or the like, and the analyte have been bound with each other by the antigen-antibody reaction. In order for each of the fluorescent dyes to be bound with the antibody, or the like, the fluorescent dye may be bound directly or may be bound via a spacer. By the use of the spacer, it is possible to adjust the position of the fluorescent dye appropriately such that the fluorescence resonance energy transfer occurs at the time at which the aforesaid antibody, or the like, and the analyte have been bound with each other by the antigen-antibody reaction.

(4) Analyte

In the present invention, the analyte, which is to be specifically bound with the reactants, should preferably be the antigen. No limitation is imposed upon the kind of the antigen, and the antigen may be selected appropriately in accordance with the purpose as the substance, which is to be detected, from various kinds of the substances which are capable of undergoing the interaction with the antibody, or the like. However, since it is necessary for the analyte to bind with the two reactants, it is necessary that the analyte has at least two sites for the binding with the reactants.

(5) Application of the Carrier for Analysis of an Analyte in Accordance with the Present Invention The carrier for analysis of an analyte in accordance with the present invention is capable of being applied to a biosensor or a bioreactor. (Reference may be made to, for example, "Bioreactor Technology," 1988, CMC K.K.; and "Biochip And Biosensor," 2006, Kyoritsu Shuppan K. K.) The term "biosensor" as used herein is interpreted in the broadest sense and means the sensor, in which an interaction between biomolecules is converted into a signal, such as an electric signal, and an object substance is thereby analyzed and detected. An ordinary biosensor is constituted of a receptor site, which recognizes a chemical substance to be detected, and a transducer site, which transduces a physical change or a chemical change, which arises at the receptor site, into an electric signal. An organism contains various combinations of substances, which have affinity with each other, such as a combination of an enzyme and a substrate, a combination of an enzyme and a coenzyme, a combination of an antigen and an antibody, and a combination of a hormone and a receptor. The biosensor utilizes the principle such that one of the substances, which have the affinity with each other, is fixed to the carrier and utilized as a molecule recognizing substance, and such that the other substance is measured selectively.

In the cases of the biosensor, to which the carrier for analysis of an analyte in accordance with the present invention is applied, a quantity of the analyte more than the corresponding quantity of each of the reactants constituting the binding product having been fixed to the carrier is not capable of binding with the reactants. Therefore, at the time at which the concentration of the analyte is detected, in order for a wide dynamic range to be taken, a time course should preferably be measured. With the measurement of the time course, the concentration in a wider region is capable of being determined from the binding speed and the binding quantity.

Also, the carrier for analysis of an analyte in accordance with the present invention is the fixation carrier. Therefore, in cases where the binding products having been formed by a plurality of kinds of the analytes are fixed respectively, each of the plurality of the kinds of the analytes forms the binding product between the corresponding first reactant and the corresponding second reactant and does not form the binding product between the first reactant and the second reactant, which do not correspond to the analyte. Therefore, the problems with regard to cross talk, which problems ordinarily occur in the cases of ELISA, and the like, do not arise, and multiple kinds of the analytes are capable of being analyzed simultaneously.

The term "bioreactor" as used herein means the reactor, in which a biochemical reaction caused to occur by a bio-catalyst, such as an enzyme, a bacterium, a cell, or an organelle, is utilized for the production of a useful substance, the generation of energy, the decomposition of an environmental pollution substance, and the like. In the cases of a bioreactor capable of performing the formation of a useful substance, the reaction, or the like, by use of an insoluble carrier, to which an enzyme has been fixed (as described in, for example, Japanese Utility Model Publication No. 4 (1992)-18398 or 4 (1992)-18399), it is possible to apply the carrier for analysis of an analyte in accordance with the present invention as the insoluble carrier.

The carrier for analysis of an analyte in accordance with the present invention will further be illustrated by the following non-limitative examples.

EXAMPLES

Example 1

<Preparation of a Support Having an Amino Group>
(Washing of the Support)

Slide glass (supplied by Matsunami Glass Ind., Ltd.) having been irradiated to UV light was dipped in acetone and subjected to an ultrasonic washing operation for five minutes. Thereafter, the slide glass was taken out from acetone and washed with pure water.
(Impartment of the Amino (APS) Group)

After 72 ml of ethanol and 8 ml of pure water were mixed together in a 100 ml glass vial, the resulting mixed solution was heated in a thermostatic chamber (supplied by AS ONE Corporation) at a temperature of 60° C. for approximately 15 minutes. The mixed solution of ethanol and pure water was thus warmed. Thereafter, 80 μl of APS (i.e., γ-aminopropyl-triethoxysilane, supplied by Tokyo Chemical Industry Co., Ltd.) was mixed with the thus warmed mixed solution of ethanol and pure water (0.1% v/v) and was dissolved in the warmed mixed solution. The slide glass having been washed was dipped in the resulting solution and was allowed to react with the solution in the thermostatic chamber (supplied by AS ONE Corporation) at a temperature of 60° C. for 15 minutes. The slide glass, to which the APS group had been imparted, was thus obtained. After the reaction had been completed, the slide glass was taken out from the solution and was washed by processing, wherein the slide glass was dipped in a solution containing ethanol and pure water in a ratio of 9:1 and was then taken out from the solution. The washing processing was performed three times. The slide glass having thus been washed was subjected to nitrogen blowing and was baked at a temperature of 120° C. for one hour. The slide glass having thus been baked was subjected to a dipping and washing operation with ethanol and the dipping and washing operation with pure water, in this order.
<Activating Esterification of CMD>

A CMD solution was prepared with processing wherein CMD (i.e., carboxymethyl dextran, molecular weight: 1,000,000, supplied by Meito Sangyo Co., Ltd.) was dissolved in ultra pure water so as to have a concentration of 0.5% by weight. Thereafter, a mixed solution, which contained 0.4M of EDC (i.e., 1-(3-dimethylaminopropyl)-3-ethylcarbodiimide) and 0.1M of NHS (i.e., N-hydroxysuccinimide), was added to the CMD solution. The mixed solution was added in a stoichiometric quantity having been calculated such that, in cases where the entire quantity had undergone the reaction, 2% of the carboxyl group might be activated. The resulting reaction mixture was stirred at the room temperature for five minutes.
<Preparation of a CMD Film>

The CMD solution having been subjected to the activating esterification was added little by little onto the support, on which the amino group had been formed. The CMD solution was then removed after a period of time of 30 seconds. In this manner, a thin film of carboxymethyl dextran having been subjected to the activating esterification was formed on the support having the amino group. After being allowed to undergo the reaction at the room temperature for one hour, the thin film was washed one time with 0.1N NaOH and was then washed one time with ultra pure water.
<Labeling of Antibodies>

A primary labeled myoglobin antibody was prepared by processing, wherein 1 mg of a myoglobin primary antibody (10-M50c, supplied by Fitzgerald Industries International, Inc.) was labeled by use of Alexa Fluor (registered trademark) 555 (supplied by Molecular Probes, Inc.) and in accordance with a procedure recommended by the supplier. Also, a secondary labeled myoglobin antibody was prepared by processing, wherein 1 mg of an antibody myoglobin secondary antibody (10-M50d, supplied by Fitzgerald Industries International, Inc.) was labeled by use of Alexa Fluor (registered trademark) 647 (supplied by Molecular Probes, Inc.) and in accordance with a procedure recommended by the supplier.
<Fixation of the Antibodies>

The thus prepared primary labeled myoglobin antibody, the thus prepared secondary labeled myoglobin antibody, and myoglobin (10-M50, supplied by Fitzgerald Industries International, Inc.) were mixed together in a molar ratio of 1:1:1. The resulting mixture was adjusted to a concentration of 0.1 mg/ml by a pH4.5 acetate buffer (supplied by Biacore). Thereafter, 10 μl of the mixture was fixed to the CMD film described above by use of Biacore surface prep unit (μ flow path), which was an option of Biacore3000 (supplied by GE Healthcare). At this time, activation was performed for seven minutes by use of 70 μl of a 0.2 M EDC/0.04 M NHS mixed activation liquid (supplied by GE Healthcare). Thereafter, a washing operation was repeated five times with PBS (phosphoric acid buffered physiological saline, supplied by Invtrogen Co.), 10 mM NaOH (supplied by Wako Pure Chemical Industries, Ltd.), and a pH2.0 glycine buffer (supplied by GE Healthcare).

Thereafter, fluorescence measurement was made on the CMD film by use of FLA-8000 (supplied by FUJIFILM Corporation), and a ratio between an intensity of emitted light having wavelengths in the vicinity of 570 nm and the intensity of the emitted light having the wavelengths in the vicinity of 675 nm was obtained. Thereafter, 0.1 mg/ml myoglobin (in a PBS buffer) was added for three minutes onto the CMD film, and pure water was poured onto the CMD film. After the pouring of pure water had been performed, the fluorescence measurement was made on the CMD film by use of FLA-8000, and the ratio between the intensity of the emitted light having the wavelengths in the vicinity of 570 nm and the intensity of the emitted light having the wavelengths in the vicinity of 675 nm was obtained. The thus obtained ratio between the intensity of the emitted light having the wavelengths in the vicinity of 570 nm and the intensity of the emitted light having the wavelengths in the vicinity of 675 nm was divided by the ratio between the intensity of the emitted light having the wavelengths in the vicinity of 570 nm and the intensity of the emitted light having the wavelengths in the vicinity of 675 nm, which ratio was obtained before the addition of myoglobin was performed. A calculation was thus made to find a rate of alteration in emitted light intensity ratio before the addition of myoglobin was performed and after the addition of myoglobin was performed. The results listed in Table 1 below were obtained.

Example 2

After the fluorescence measurement was made as in Example 1, a washing operation with a pH2.0 glycine buffer and a washing operation with 10 mM NaOH were alternately repeated five times. Thereafter, in the same manner as that in Example 1, the addition of 0.1 mg/ml myoglobin (in a PBS buffer) was performed, and the calculation was made to find the rate of alteration in emitted light intensity ratio before the addition of myoglobin was performed and after the addition of myoglobin was performed.

Comparative Example 1

Fixation of the antibodies was performed in the same manner as that in Example 1, except that, in lieu of the mixture solution of the primary labeled myoglobin antibody, the secondary labeled myoglobin antibody, and myoglobin being used in the step of <fixation of the antibodies> in Example 1, a mixture of only the primary labeled myoglobin antibody and the secondary labeled myoglobin antibody (without myoglobin) was used. Thereafter, in the same manner as that in Example 1, the addition of 0.1 mg/ml myoglobin (in a PBS buffer) was performed, and the calculation was made to find the rate of alteration in emitted light intensity ratio before the addition of myoglobin was performed and after the addition of myoglobin was performed.

TABLE 1

| | Rate of alteration in emitted light intensity ratio before addition of myoglobin was performed and after addition of myoglobin was performed |
|---|---|
| Example 1 | At least 3% |
| Example 2 | At least 3% |
| Comparative Example 1 | 0% |

As clear from Table 1, in Example 1 and Example 2, in which the primary labeled myoglobin antibody, the secondary labeled myoglobin antibody, and myoglobin were previously subjected to the fixation from the mixed liquid, the FRET intensity after the addition of myoglobin was performed altered. However, in Comparative Example 1, the alteration in FRET intensity was not found. It was thus found that, in the cases of the carrier for analysis of an analyte in accordance with the present invention (obtained in each of Example 1 and Example 2), with the binding product constituted of the primary labeled myoglobin antibody, the secondary labeled myoglobin antibody, and myoglobin, the primary labeled myoglobin antibody and the secondary labeled myoglobin antibody took the positions spaced by a close distance which allows the fluorescence resonance energy transfer to occur. It was also found that, in Comparative Example 1, the primary labeled myoglobin antibody and the secondary labeled myoglobin antibody were not fixed at the positions spaced by a close distance which allows the fluorescence resonance energy transfer to occur. In each of Example 1, Example 2, and Comparative Example 1, the calculation was made to find the rate of alteration in emitted light intensity ratio before the addition of myoglobin having the identical concentration was performed and after the addition of myoglobin having the identical concentration was performed. In terms of the numerical value, the difference of the rate of alteration in emitted light intensity ratio between Examples 1, 2 and Comparative Example 1 was 3%. However, in Comparative Example 1, in cases where the concentration of myoglobin was increased by a factor of 100 (to 10 mg/ml), it was not possible to detect the analyte. It was thus demonstrated that the fluorescence resonance energy transfer was applied first to the solid phase in the present invention, and the detection of the analyte was thereby made possible.

Therefore, with the carrier for analysis of an analyte in accordance with the present invention, which was produced by fixing the first reactant and the second reactant onto the support by use of the binding product constituted of the first reactant, the analyte, and the second reactant, the fluorescence resonance energy transfer is applicable to the solid phase, and therefore it is possible to perform quick in situ analysis.

Also, in Example 2, it was found that, even after the analyte washing was performed, fixation to the support was possible, and it was thus found that the analysis was capable of being made repeatedly. Therefore, with the carrier for analysis of an analyte in accordance with the present invention, it is possible to furnish the carrier for analysis of an analyte, which carrier enables an analyte to be detected quickly with a high sensitivity and in a simple manner, and which carrier has a high flexibility in application.

The invention claimed is:

1. A process for producing a carrier for analysis of an analyte, comprising the steps of:
   i) allowing an analyte, a first reactant, and a second reactant to react with one another,
      the first reactant being provided with a reaction site for specific binding with the analyte, and a fluorescent label site,
      the second reactant being provided with a reaction site for specific binding with the analyte, and a fluorescence recognition site for recognizing fluorescence produced by the fluorescent label site of the first reactant,
      a binding product of the first reactant, the analyte, and the second reactant being obtained from the reaction, and
   ii) imparting the binding product to a surface of a support of the carrier, whereby the first reactant and the second reactant are respectively fixed to the surface of the support.

2. A process for producing a carrier for analysis of an analyte as defined in claim 1 wherein, after the first reactant and the second reactant have been respectively fixed to the surface of the support, the analyte is removed from the binding product.

3. A process for producing a carrier for analysis of an analyte as defined in claim 1 wherein the removal of the analyte from the binding product is performed under conditions such that the binding of the analyte is weakened.

4. A process for producing a carrier for analysis of an analyte as defined in claim 1 wherein the analyte is removed from the binding product by altering the pH or the concentration of a salt.

5. A process for producing a carrier for analysis of an analyte as defined in claim 1 wherein the surface of the support is modified by the addition of a functional group by one of a plasma process, an ozone process, an etching process that uses an acid/an alkali, and a surface process that employs a self-assembling film.

6. A process for producing a carrier for analysis of an analyte as defined in claim 1 wherein the first reactant and the second reactant are immobilized on the surface of the support via a polymer layer after the polymer layer is formed on the surface of the support.

* * * * *